United States Patent [19]

Akiyoshi et al.

[11] Patent Number: 4,590,170

[45] Date of Patent: May 20, 1986

[54] PROCESS FOR PREPARING MICROCAPSULE REAGENTS FOR IMMUNOLOGICAL RESPONSE

[75] Inventors: Yutaka Akiyoshi; Shinzo Kobayashi, both of Tokyo; Fujio Kakimi; Hiroharu Matsukawa, both of Shizuoka, all of Japan

[73] Assignee: Fuji Photo Film Co., Ltd., Kanagawa, Japan

[21] Appl. No.: 281,529

[22] Filed: Jul. 8, 1981

[30] Foreign Application Priority Data

Jul. 9, 1980 [JP] Japan .................................... 55-93407

[51] Int. Cl.$^4$ .................... G01N 33/547; G01N 33/53
[52] U.S. Cl. .........................................436/533; 264/4.1; 264/4.33; 428/402.2; 428/402.21; 428/402.22; 436/528; 436/534; 436/829
[58] Field of Search ............... 424/3, 8, 12, 13, 33, 424/35, 37; 436/532, 533, 534, 528, 530, 531, 829, 535; 252/316; 264/4; 428/402.2

[56] References Cited

U.S. PATENT DOCUMENTS

| 2,800,458 | 7/1957 | Green . |
| 3,155,590 | 11/1984 | Miller . |
| 3,190,837 | 6/1965 | Brynko . |
| 4,021,364 | 5/1977 | Speiser .................................. 424/33 |
| 4,053,585 | 10/1977 | Allison .................................. 424/38 |
| 4,193,983 | 3/1980 | Ullman .............................. 424/3 X |
| 4,342,739 | 1/1980 | Kakimi et al. ........................ 424/32 |

FOREIGN PATENT DOCUMENTS 3000483 7/1980 Fed. Rep. of Germany .
2041517 9/1980 United Kingdom .

*Primary Examiner*—Sidney Marantz
*Attorney, Agent, or Firm*—Sughrue, Mion, Zinn, Macpeak & Seas

[57] ABSTRACT

A process for producing a microcapsule diagnostic material utilizing passive agglutination which comprises binding an antigen or antibody onto a microcapsule wall negatively charged, in an acidic solution is provided. The microcapsule diagnostic material thus produced has an extremely high sensitivity in agglutination without causing any non-specific agglutination.

13 Claims, No Drawings

PROCESS FOR PREPARING MICROCAPSULE REAGENTS FOR IMMUNOLOGICAL RESPONSE

BACKGROUND OF THE INVENTION

1. Field of the Invention

The invention relates to a process for preparing microcapsule reagents suitable for immunological response, more particularly, to a process for preparing microcapsule reagents suitable for an antigen-antibody response which have high sensitivity, are stable and cause non-specific agglutination only with difficulty.

2. Development of the Invention

In order to facilitate an antigen-antibody response of high sensitivity in a simple manner, an immunological agglutination method in which an antigen or antibody is carried on a water-insoluble carrier and which causes agglutination based on an antigen-antibody response which can be seen with the naked eye has been employed.

Red blood cells of animals such as chickens, alligators, sheep, etc., have been used as carriers for the antigens or antibodies and, utilizing these carriers, passive heamagglutination (PHA) has generally been used since this method provides high sensitivity with simple operations.

Recently, a method has been used for semi-qualitatively determining the presence or absence of antigens or antibodies very efficiently in a simple manner which is called the microtiter system. However, the microtiter system involves disadvantages, e.g., due to the use of animal-originated carriers, red cell carriers per se are antigenic and often cause specific agglutination to adversely affect the desired antigen-antibody response: further, efficiency is not uniform based on differences between subjects, changes with the passage of time and cost is high.

A latex agglutination method in which a polystyrene latex is used as a carrier has also been put into practical use. While the disadvantages encountered with the use of animal-originated carriers is eliminated by this method, this method also involves disadvantages, e.g., not only is sensitivity poor as compared to the passive haemagglutination method, but storability over long periods of time is poor because of weak bonding with an antigen or antibody. Further, natural agglutination—not based on an antigen-antibody response—tends to occur, etc.

In U.S. Pat. No. 4,342,739, microcapsules are suggested for use in place of conventional carriers for immune substances, such as the aforesaid red cells, latexes, etc., for antigen-antibody agglutination. In the case microcapsules are employed as carriers, a marked improvement in sensitivity and accuracy is generally recognized in the detection of various antibodies or antigens in specimens based on antigen-antibody agglutination. This is due to the fact that microcapsules having a desired specific gravity of 0.8 to 1.20, preferably 1.07 to 1.16, can be prepared in a desired particle size range of 0.1 to 30 microns, preferably 0.5 to 10 microns, by suitably choosing the core substance(s) of the microcapsules. The microcapsules proposed in U.S. Pat. No. 4,342,739 are not charged (zero charge) or are positively charged in the acidic pH area.

However, some antigens or antibodies are sensitized only with extreme difficulty and a method for preparing reagents capable of utilizing such antigens or antibodies has long been desired in the art.

SUMMARY OF THE INVENTION

It has now been found that if upon binding an antigen or an antibody to a microcapsules the pH of the reaction liquid is adjusted to the acidic area and microcapsules negatively charged in this pH area are employed, an antigen or antibody can easily be bound to the wall of the microcapsules, whereby a method of preparing reagents of high sensitivity and stability is provided.

The microcapsules used in accordance with the present invention which are negatively charged in the desired pH area can be prepared by the presence of a negatively charged substance in an oily substance used as the core substance(s) of the microcapsules or alternatively by using a negatively charged substance in the walls and/or on the wall surface of the microcapsules.

The term "microcapsule" used herein refers to a microcapsule comprising a wall material having encapsulated therein an oily substance as the core.

The terms "wall material" and "core" or "core material" as used hereafter are all established in the art, as are seen in, e.g., U.S. Pat. Nos. 4,087,376, 4,089,802 and 4,100,103, British Pat. No. 53,170 and T. Kondo, *MICROENCAPSULATION* - New Technique And Application, published by Techno Books, New York, (1979).

DESCRIPTION OF THE PREFERRED EMBODIMENTS

Typical examples of negatively charged substances i.e., compounds which can be used for preparing negatively charged microcapsules used in the present invention include high molecular weight substances containing an anionic group(s) in the side chain thereof.

Specific examples of anionic groups are, for example, a sulfonic acid group, a sulfone group, a carboxylic acid group, a maleic acid group, or alkali metal (e.g., Na or K) salts thereof. The molar ratio of monomers containing the aforesaid anionic groups therein to monomers free of anionic groups is generally in a range from about 10 to 60 mol %.

It is preferred that the molecular weight of the high molecular weight substances be in a range from about 10,000 to about 1,000,000, since if the molecular weight is too low, viscosity is too low to effect encapsulation whereas and if the molecular weight is overly high, the viscosity is so high that emulsification occurs only with difficulty. High molecular weight substances containing $-SO_3H$ as anionic groups are relatively highly soluble in water. Accordingly, it is desired to use such substances having a molecular weight of about 100,000 to about 1,000,000, in order to ensure a viscosity sufficient to effect emulsification. As compared to such $-SO_3H$-containing high molecular weight substances, high molecular weight substances containing $-COOH$ as anionic groups can cause emulsification as well as emulsification successfully even with a molecular weight ranging from about 10,000 to about 300,000. In any event, control of molecular weight in relation to emulsification and encapsulation is completely obvious to one skilled in the art of microencapsulation.

Specific examples of high molecular weight substances which can be employed in the present invention include polyvinyl sulfates, polyvinyl sulfonates, polystyrene sulfonates, polyacrylic acids, maleic anhydride copolymers (for example, maleic anhydride-methyl vinyl ether copolymers, maleic anhydride-isobutylene copolymers, maleic anhydride-ethylene copolymers, maleic anhydride-styrene copolymers) and alkali metal (e.g., Na or K) salts thereof. When copolymers are employed, it is preferred that anionic group-containing monomers be contained in an amount of about 10 to 60 mol % to monomers free of anionic groups.

The amount of one or more of these substances used in the preparation of the microcapsules is generally in the range of 2 to 50 wt % based on the weight of the oily substance which constitutes the core.

The microcapsules in accordance with the present invention are each individually highly negatively charged so that microcapsule aggregation is prevented due to electrostatic repellency; as a result, the stability of the system is maintained and non-specific agglutination—agglutination which is not based on an antigen-antibody response—occurs only with difficulty. For these reasons, it is possible to bind an antigen or antibody onto the wall surface of the microcapsule particles in a relatively higher concentration, as compared to the case in which substances free from any anionic group are employed for the preparation of microcapsules as is observed in Table 2 hereinafter, and, as a result, microcapsules having an antigen or antibody bound thereto can respond to even a trace amount of an antibody or antigen with high sensitivity to thereby cause an immunological agglutination, resulting in extremely high detection sensitivity.

Any substance(s) can be employed for the wall substance(s) of the microcapsule used in the present invention as long as they are capable of chemically binding an antigen or antibody thereto without damaging the activity of the antigen or antibody and are capable of encapsulation. Typical examples of wall substances include wall substances containing an amino group or an imino group, e.g., proteins (such as collagen, gelatin, casein, etc.), polyamino acids, polyacryl amides, polyamides, polyurethanes, polyureas, melamines, etc.; wall substances containing a hydroxy group therein such as cellulose and derivatives thereof (e.g., methyl cellulose, ethyl cellulose, carboxymethyl cellulose, etc.), gum arabic, starch, etc.

The wall thickness is conventional and varies depending upon raw materials, utility, purpose, etc., but generally is in the range of about 100 to about 300 nm.

As oily substances which are sparingly soluble in water and non-volatile liquids at room temperature, and form the core of the microcapsules, natural mineral oils, animal oils, plant oils and synthetic oils can be employed in the present invention. These core substances are completely enclosed by the capsule walls and hence do not directly affect an antigen or antibody due to their properties.

Preferred examples of mineral oils include petroleum, kerosene, gasoline, naphtha, paraffin oils, etc. Preferred examples of animal oils include fish oil, lard, etc. Preferred examples of plant oils include peanut oil, linseed oil, soybean oil, castor oil, corn oil, etc. Examples of synthetic oils are biphenyl compounds (e.g., isopropyl biphenyl, isoamyl biphenyl), terphenyl compounds (e.g., compounds as described in W. German OLS No. 2,153,635), naphthalene compounds (e.g., diisopropyl napthalene, compounds as described in U.S. Pat. No. 4,003,589), alkylated diphenylalkanes (e.g., 2,4-dimethyldiphenylmethane, compounds as described in U.S. Pat. No. 3,836,383), phthalic acid compounds (e.g., diethyl phthalate, dibutyl phthalate, dioctyl phthalate), etc.

Core materials for the microcapsules which can be employed in the present invention are not limited to the compounds described above.

In addition to the aforesaid negatively charged substances present in the core material, oil-soluble dyestuffs can also be incorporated into the core material for the purpose of improving contrast in agglutination in an amount of 0.05 to 10 wt %, preferably 0.1 to 5 wt %. While not overly limited, examples of useful oil-soluble dyes include dyes having Colar Index Nos. 12010, 12150, 12715, 12716, 13900, 26100, 26105, 26110, 26125, 27291, 45170, 60505, etc.

The core material(s) for the microcapsules in accordance with the invention can also contain marking substances such as an isotope, a fluorescent substance, a magnetic substance, an ultraviolet substance, etc., in an amount of 0.05 to 10 wt %, preferably 0.1 to 5 wt %. (U.S. Pat. No. 4,342,739).

Methods for preparing microcapsules used in the present invention are not particularly limited, and conventional methods can be employed, for example, as described in T. Kondo, *MICROENCAPSULATION*- New Technique And Application, published by Techno Books, New York (1979), A. Kondo, *MICROCAPSULE*, Nikkan Kogyo Press, Tokyo (1970), Tamotsu Kondo and Masumi Koishi, *MICROCAPSULE*, Sankyo Publishing Co., Ltd., Tokyo (1972), U.S. Pat. Nos. 4,087,376, 4,089,802 and 4,100,103, British Pat. No. 53,170, etc.

It is preferred that the specific gravity of microcapsules used in the present invention range from about 0.80 to about 1.20. Such can be altered by appropriately choosing the core material as taught in U.S. Pat. No. 4,342,739.

It is preferred that the average particle size of the microcapsule be in a range of from 0.1 to 30 microns, more preferably 0.5 to 10 microns.

To determine the negative charge of the microcapsules used in this invention, a zeta potential measurement method, a dye absorption method, a colloid titration method, etc., can be used. Details of these methods are described in B. Jirgensons and M. E. Straumanis, *A SHORT TEXTBOOK OF COLLOID CHEMISTRY* second revised ed., Pergamon Press, pages 127-155 (1962), A. W. Adamson, *PHYSICAL CHEMISTRY OF SURFACE*, third ed., pages 208-216, Joh,-Willy & Sons, Inc. (1976), and *CELL MEMBRANE IN CANCER* edited by Hiroshi Terayama, pages 20-59 (1978), published by Nankodo Publishing Co., Tokyo, and incorporated by reference.

Of these methods, a representative method which has been widely employed in the art is a zeta potential measurement method. According to this method, the microcapsules are negatively charged to a zeta potential more negative than —20 mV; a preferred range for the zeta potential is between —20 and —80 mV, more preferably —40 and —60 mV.

To bind an antigen or antibody to a microcapsule, various conventional methods can be employed, e.g., an aldehyde cross linking method, an alkylation method, a cyanobromide method, a maleimide cross linking method, etc.; details thereon are given in *METHODS IN ENZYMOLOGY* edited by K. Mososhack, vol. 44, entitled "Immobilized Enzyme", published by Academic Press (1976), S. J. Gutcho, *IMMOBILIZED ENZYMES*, entitled "Preparation And Engineering Techniques", published by Noyesdata Co., Ltd. (1974), and *KOTEIKA KOSO* (Immobilized Enzyme), published by Kodansha Publishing Co., Ltd. (1975), pages 10–44, which are hereby incorporated by reference. While the binding methods selected are not limitative, it is important that the antigens or antibodies bound not be inactivated.

The most typical binding method is binding using an aldehyde such as glutaraldehyde, formaldehyde, glyoxal, etc. According to this method, the microcapsules are mixed with, e.g., glutaraldehyde, at a temperature of about 15° to about 40° C., preferably at room temperature (18°–28° C.), for about 1 to about 2 hrs. under normal pressure, and the mixture is washed with distilled water to remove unreacted aldehyde. Then the aldehydetreated microcapsule slurry is mixed with about 0.005 to 0.2 wt % antigen or antibody based on a solid content (the wall and the core) of the slurry, followed by reaction at room tempreature (18°–28° C.) for 1 to 2 hrs.

The binding or cross linking agents are not limited to aldehydes and additional representative binding agents include water-soluble carbodiimides such as 1-ethyl-3-(3-dimethylaminopropyl)carbodiimide hydrochloride, 1-cyclohexyl-3-(2-morpholinyl-4-ethyl)carbodiimide methyl p-toluenesulfonate; isoxazolium salts such as N-ethyl-5-phenylisoxazolium-3'-sulfonic acid, imide esters such as diethyl maloneimidate, N,N',O-phenylenedimaleimide, m-maleimidobenzoyl, N-hydroxysuccinimide; diisocyanates such as toluene 2,4-diisocyanate; halonitrobenzenes such as p,p'-difluorom,m'-dinitrophenylsulfone; alkyl chloroformates such as ethyl chloroformate, etc. However, the binding or cross linking agents are not limited thereto.

Representative examples of immunologically active substances which can be bound onto the wall surface of the microcapsule in accordance with this invention to cause an antigen-antibody response include peptide hormones such as hypothalamus hormones (e.g., TRH, LH-RH, somatostatin), hypophysis hormones (e.g., growth hormone, ACTH, $\alpha$-MSH, $\beta$-MSH, lipotropin, prolactin, TSH, TSH-$\beta$, LH, LH-$\beta$, FSH, FSH-$\beta$, $\alpha$-subnit, arginine vasopressin, lysine vasopressin, oxytocin, etc.), calcium metabolism regulating hromones (e.g., insulin, proinsulin, C-peptide, glucagon, etc.), digestive tract hormones (e.g., gastrin, secretin, pancreozymincholecystokinin, GIP, enteroglucagon, etc.), hormones acting on blood vessels (e.g., angiotensin I, angiotensin II, bradykinins, etc.), placental hormones (e.g., human chorionic gonadotropin (HCG), HCG-$\beta$, human chorionic somatomommatropin, human chorionic thyrotropin), non-peptide hormones such as steroids (e.g., cortisol, corticosterone, 11-deoxycortisol, 11-deoxycroticosterone, progesterone, 17-hydroxyprogesterone, pregnenolone, aldosterone, testosterone, dihydrotestosterone, estradiol, estriol, estrone, 2-hydroxyestrone, dehydroepiandrosterone, etc.), thyroid hormones (e.g., thyroxine, 3,5,3'-triiodothyronine 3,3',5'-triiodothyronine etc.), prostaglandins (e.g., prostaglandin A, E, F, etc.); substances other than hormones such as drugs (e.g., digoxin, digitoxin, morphine, LSD, gentamycin, amphetamine, nicotine, etc.), cyclic nucleotides (e.g., cyclic AMP, cyclic GMP, cyclic IMP, cyclic UMP, etc.), enzymes (e.g., $C_1$ esterase, fructose 1,6-diphosphatase, alkaline phosphatase, dopamine beta hydroxylase, pepsinogen, etc.), virus specific antigens (e.g., hepatitis B virus, murine sarcomaleukemia virus, wooly monkey leukemia virus, avian tumor virus, plant virus, avian C-type virus, etc.), tumor antigens (e.g., $\alpha$-fetoprotein, CEA, etc.), blood serum proteins (e.g., thyroxin binding globulin (TBG), IgG, IgM, IgE, IgA $\alpha_2$-microglobulin, properdin, anti-Rh antibodies, transferrin, aplipoprotein, fibrinogen degradation products, antihaemolytic factor, renin, etc.); rheumatism factor, folic acid, neurophysin, somatomedin B, nerve growth factor, epidermal growth factor, staphylococcal enterotoxin A and B, type A toxin of chlostridium botulinum, myosin, encephalitogenic basic proteins, substance P, serotonin, conjugated cholyl bile acid, $H_{BS}$-antigen, etc.

Of these immunologically active substances, those which are particularly preferably bound onto the wall surface of the microcapsules in this invention are IgG, IgM, IgE, IgA, insulin, $H_{BS}$-antigen, $\alpha$-fetoprotein, human growth hormone, renin, gastrin LH, FSH, cortisol, angiotensin, ACTH, C-peptide, CEA, glucagone, and aldosterone.

The process in accordance with this invention includes three basic embodiments.

A first embodiment comprises binding the aforesaid binding or cross linking agent onto the wall surface of a microcapsule and thereafter reacting an antigen or antibody therewith in an acidic solution, generally at a pH of from about 3.0 to 5.5, preferably 4 to 5.5, to thereby bind the antigen or antibody to the microcapsule wall through the binding or cross linking agent.

A second embodiment comprises reacting an antigen or antibody with the aforesaid binding or cross linking agent and a then binding the microcapsule wall thereto in an acidic solution having a pH as described above.

A third embodiment comprises bringing an antigen or antibody, the aforesaid binding or cross linking agent and microcapsule into contact in an acidic solution having a pH as described above, where reactions of the cross linking agent with the antigen or antibody and with the microcapsule wall are simultaneously caused.

Procedures for binding antigens or antibodies with microcapsule walls in accordance with this invention will now be described in more detail.

A microcapsule slurry is diluted with a saline solution to a 1 to 3 wt % solid content (the core and the wall) based on the total weight of the slurry.

A cross linking agent, e.g., glutaraldehyde, is added to the thus diluted microcapsule slurry in an amount of 0.1 to 50 wt % based on the solid content of microcapsules. The resulting mixture is incubated at a temperature of room temperature to 65° C. for 5 to 60 mins. to react the cross linking agent with the functional groups on the microcapsule walls. After residual cross linking agent is removed by washing by means of centrifugal separation, the resulting dispersion is adjusted to an acidic pH, preferably a pH of 3.0 to 5.5, using a buffer solution having such a pH value, or the resulting dispersion is often in a pH range of 4 to 5.5 and, in this case, no adjustment is needed, of course. An antigen or antibody is added to the dispersion in an amount of 0.1 to 25 wt % based on the solid content of microcapsules. The mixture is incubated at 37° C. for 30 to 120 mins. to react the antigen or antibody with remaining functional groups of the glutaradehyde bound to the microcapsule walls. Unreacted antigen or antibody is removed by washing by means of centrifugal separation. Any functional groups of the glutaraldehyde, a part of which is bound to the microcapsule walls and the other part of which remain unreacted, are further reacted with a glycine solution by dispersing the system in the glycine solution and incubating the dispersion at 37° C. for 30 mins., or by simply washing the system with the glycine solution at 37° C. Thus, the unreacted functional groups of the glutaraldehyde are completely blocked and hence any undesired non-specific immune reaction can be avoided.

While it varies depending upon kind of antigen or antibody, or kind of microcapsules, the amount of antigen or antibody which is actually bound to the microcapsules is at least 10 wt % based on the total weight of the antigen or antibody employed, ordinarily about 25 to about 40 wt %, same basis. This is surprising if one considers the fact that the amount of antigen or antibody which is bound to microcapsules containing no anionic groups (i.e., conventional microcapsules) is 1 wt %, same basis, at the maximum.

The diagnostic materials obtained in accordance with this invention are characterized by extremely high sensitivity in agglutination, by the fact that non-specific agglutination occurs only with difficulty, by the fact that they can be stably stored over long periods of time and manufactured easily with uniform quality on an industrial scale, by the fact that antigens or antibodies useful therewith can be selected from an extremely wide range, by the fact that an oily substance is employed as the core of the microcapsule which renders encapsulation easier, and by the fact that the surface of the microcapsule is uneven which results in enlarged surface area, as compared to singlephase particles which possess a smooth surface, etc., i.e., they are extremely useful from diagnostic and preparational viewpoints.

The invention will now be described in detail with reference to the examples below, but is not deemed to be limited thereto. Unless otherwise indicated, all percentages are by weight and all reactions were at room temperature (18° to 28° C.) and ambient pressure.

In the examples below, the term "solids content" refers to the content of the core and the wall.

EXAMPLE 1

(1) Preparation of Microcapsule A

In 25 g. of a 5% aqueous solution of sodium polystyrene sulfonate (degree of sulfonation, 100%; molecular weight, 500,000), a mixture (specific gravity, 1.10) of 11.8 g. of diisopropyl naphthalene containing 0.1 g. of Aisen Spiron Red (trademark, made by Hodogaya Chemical Co., Ltd., an oil-soluble red dye) and 13.2 g. of chlorinated paraffin (degree of chlorination, 50%) was emulsified to prepared an emulsion having an average oil droplet size of W,6 μm.

Separately, an aqueous mixture of 1.5 g. of melamine, 2.5 g. of a 37% aqueous formaldehyde solution and 21 g. of water was heated at 60° C. for 30 mins. to dissolve. The resulting solution was added to and mixed with the emulsion obtained above. After adjusting the pH to 6.0 with 1N hydrochloric acid, the mixture was reacted at 60° C. for about 2 hrs. After completion of the reaction, the system was adjusted to pH 9.0 with a 20% aqueous sodium hydroxide solution to prepare microcapsules. The thus prepared microcapsule slurry was centrifuged three times with a saline solution to remove the remaining formaldehyde, etc. Thereafter, the microcapsules were dispersed in a saline solution at a solids content of 10% (Microcapsule A).

(2) Preparation of Microcapsule B

To 25 g. of a 10% aqueous solution of maleic anhydridemethyl vinyl ether copolymer (GANTREZ-AN 139, trademark, made by General Aniline & Film Co., Ltd.; molecular weight, ca. 25,000), 2.5 g. of urea, 0.25 g. of resorcin and 0.3 g. of ammonium chloride were added. To the resulting mixture, a mixture (specific gravity, 0.10) of 11.8 g. of diisopropyl naphthalene containing 0.1 g. of an oil-soluble red dye (Aisen Spiron Red, trademark, made by Hodogaya Chemical Co., Ltd.) and 13.2 g. of chlorinated paraffin (degree of chlorination, 50%) was added. The thus obtained mixture was then emulsified to prepare an emulsion having an oil droplet size of 6 μm. After adjusting the pH of the emulsion to 4.0, 6.7 g. of a 37% aqueous formaldehyde solution was further added to the emulsion. The resulting mixture was heated at 60° C. for 2 hrs. After heating, the pH of the system was adjusted to 9.0 with a 20% aqueous sodium hydroxide solution to obtain a microcapsule slurry. After washing the microcapsule slurry three times by centrifuging with a saline solution, the microcapsules were dispersed in a saline solution to a solids content of 10% (Microcapsule B).

(3) Preparation of Microcapsule C

A microcapsule dispersion (Microcapsule C) was prepared in a manner similar to (2) above except that 25 g. of a 10% aqueous solution of polyvinyl alcohol (degree of saponification, 90%; degree of polymerization, 500) was employed in place of the maleic anhydridemethyl vinyl ether copolymer used in the preparation of Microcapsule B.

(4) Preparation of Microcapsule D

In 40 g. of warm water (40° C.), 5 g. of acid-treated gelatin and 5 g. of gum arabic dissolved. In the solution, 50 g. of an oil mixture (specific gravity, 1.10) as employed in the preparation of Microcapsule A was emulsified to prepare an emulsion having an average oil droplet size of 6.0 μm.

To the emulsion, 213 g. of water at 40° C. was added. Thereafter, the pH of the mixture was adjusted to 4.6 with acetic acid. After cooling the system to 10° C., 2 g. of a 37% formaldehyde aqueous solution was added to the system to harden the microcapsule walls. After further adding 40 g. of a 10% carboxymethyl cellulose (degree of polymerization, 220) aqueous solution to the system, the pH of the resulting mixture was adjusted to 10 with a 10% aqueous sodium hydroxide solution. Thereafter, the temperature of the system was elevated to 50° C., at which temperature the system was stirred for 1 hr. and then allowed to stand. The thus obtained gelatin wall microcapsule slurry was washed three times with a saline solution by centrifugation to remove the remaining formaldehyde, etc. The system was then dispersed in a saline solution to a solids content of 10% (Microcapsule D).

(5) Preparation of Microcapsule E

A microcapsule dispersion (Microcapsule E) was prepared in a manner similar to the preparation of Microcapsule B except that 5 g. of a 10% aqueous solution of maleic anhydride-methyl vinyl ether copolymer ("GANTREZ-AN 139", trademark, made by General Aniline & Film Co., Ltd.; molecular weight, ca. 25,000) was employed.

Measurement of Zeta Potential

The zeta potentials of Microcapsules A through E prepared as described above were determined using a ZPOM-METER manufactured by Kyowa Kagaku Co., Ltd. Specifically, a fixed voltage of 50 volts was applied to a cell for electrophoretic measurement equipped with a quartz capillary and electrodes spaced 10 cm. apart from the capillary. The mobility of the microcapsules was then observed with a microscope to measure the time period in which the microcapsules moved a distance of 100 μm. Electrophoretic mobility was then determined by the following equation:

$$V \text{ (electrophoretic mobility)} = \frac{\text{distance moved (0.01 cm)}}{\text{time required to move (sec.)}} \Big/ \text{slope of potential} \left(\frac{50 \text{ V}}{10 \text{ cm}}\right)$$

The relationship between the zeta potential and electrophoretic mobility V follows the following equation, in which zeta potential was calculated based on the value of V where the viscosity and dielectric constant of the liquid tested were considered to be constant since the liquid tested was a 500-fold dilution.

$$\text{Zeta Potential } (mV) = 4\pi \frac{\text{(viscosity of liquid)}}{\text{(dielectric constant of liquid)}} \times \left(\text{electrophoretic mobility } \frac{cm^2}{V \cdot sec.}\right) = 14.13 \times 10^4 \times V$$

The microcapsules were subjected to measurement per the above procedure by diluting them with an aqueous dihydrogen potassium phosphate solution [1/100 mol concentration (pH 4.6)] to a solids content of 0.04%.

The zeta potentials of Microcapsules A, B, C, D and E prepared in Example 1 are shown in Table 1.

TABLE 1.

| Microcapsules | Zeta Potential of Microcapsules | | | | |
|---|---|---|---|---|---|
|  | A | B | C | D | E |
| Zeta Potential (mV) | −57 | −75 | ≈0 | ≈0 | −48 |

Microcapsules A, B and E possess zeta potentials more negative than −20 mV.

Microcapsules C and D are considered to be almost substantially stationary in a solution having pH of 4.6 as above described, in the case where it takes 15 secs. or more for the microcapsules to move 100 μm between standard lines. In this case, the zeta potential of the particles is −19 mV.

EXAMPLE 2

Sensitization of FITC-Marked Human IgG

A 1.5 g. sample of each of Microcapsules A, B, C, D and E was taken and dispersed in 10 ml. of a saline solution, respectively. The dispersion was mixed with 100 μl. of glutaraldehyde and the mixture then reacted for 1 hr. at room temperature. After completion of the reaction, the reaction mixture was washed with a saline solution using a centrifuge and the resulting precipitate dispersed in 10 ml. of a phosphate-citrate buffer solution of pH 4.2.

Then, a 1% solution of anti-human IgG (caprinized) (made by Igaku Seibutsugaku Research Laboratories) marked with a fluorescent substance, FITC (short for fluoresscein isothiocyanate) was diluted 25 times (by volume) with a saline solution. To 2 ml. of samples (microcapsules: 30 mg/ml.) of Microcapsules A, B, C, D and E treated with glutaraldehyde which were in the buffer solution, 1 ml. of the diluted FITC-marked anti-human IgG was added, respectively, followed by incubation at 37° C. for 1 hr. The system was then further allowed to stand at 4° C. for 15 hrs.

After centrifugal separation, the supernatant was taken out as a sample. The relative fluorescein intensity of the sample was determined using a spectrophotofluorometer Model 650 manufactured by Hitachi Ltd., in which the wavelength of excited light Ex=480 nm and the wavelength of measuring radiated light Em=520 nm were employed.

A solution of diluted anti-human IgG employed for the sensitization was further diluted with a saline solution in a 1:2 ratio (same anti-human IgG:saline solution). The percentage of fluorescein intensity of the supernatant after sensitizing with microcapsules with respect to the fluorescein intensity of the anti-human IgG dilution was determined. The results are shown in Table 2.

TABLE 2.

| Microcapsules | Relative Fluorescein Intensity of Supernatant After Sensitization | | | | |
|---|---|---|---|---|---|
|  | A | B | C | D | E |
| Relative Fluorescein Intensity (%) | 3 | 5 | 93 | 91 | 6 |

With Microcapsules A, B and E, most of anti-human IgG add was present in the precipitate remaining after centrifugal separation, i.e., bound anti-human IgG in the precipitate; whereas most of anti-human IgG remained in the supernatant with Microcapsules C and D, i.e., the same failed to bind with the microcapsules.

After further washing twice with a saline solution containing 0.2% glycine, the precipitate was dispersed in a 0.15M phosphate buffer-saline solution (PBS, pH=7.2) containing 2 ml. of 3% bovine serum albumin to prepare a reagent for detecting IgG.

100 μl of the thus prepared reagent was taken and diluted with 2 ml. of a saline solution. The relative fluorescein intensity of the dilution was measured using a spectrophotofluorometer Model 650 manufactured by Hitachi Ltd.

Separately, a calibration curve was prepared. Using the calibration curve, the amount of anti-human IgG bound to the microcapsules was quantitatively determined. Thus, the percentage to the anti-human IgG added was then determined.

The results are shown in Table 3.

TABLE 3.

| Microcapsules | Anti-Human IgG Bound to Microcapsules | | | | |
|---|---|---|---|---|---|
|  | A | B | C | D | E |
| Rate of Sensitization of Anti-Human IgG (%) | 34 | 32 | 0 | 0 | 23 |

As can be seen from the results shown in Table 3, approximately ⅓ of the anti-human IgG added was bound to Microcapsules A and B and approximately ¼ to Microcapsule E whereas the anti-human IgG was hardly bound to Microcapsules C and D.

Immunological agglutination was then caused between the anti-human IgG-sensitized microcapsule reagents and human IgG using a microtiter method. A cell in which agglutination could be clearly observed was made positive, and the maximum double dilution of human IgG was determined and made the anti-body titer (see *A DICTIONARY OF IMMUNOLOGY*, edited by W. J. Herbert and P. C. Wilkinson, Blackwell Scientific Publications, Oxford and Edinburgh, page 57).

A 1% saline solution of human IgG (GAMMA GLOBULIN HUMAN FR II, trademark, made by ICN Pharmaceuticals Inc.) and normal rabbit serum as a control were diluted 20 times by volume with a 0.15M phosphate buffer-saline solution (PBS, pH=7.2). 25 μl. of the thus obtained dilution liquids were put in respective cells on a microplate. The dilution liquids were further diluted with a phosphate buffer-saline solution in a doubling serial dilution to prepare a doubling dilution series.

Next, anti-human IgG-sensitized Microcapsules A, B, C, D and E prepared in the aforesaid manner were taken out with a dropper in 25 μl. samples of each; that is, to dilute the system serially, 25 μl. of one sample was added to one cell. The contents were mixed and 25 μl. was taken and added to a second cell. The procedure was repeated to the end of a row of cells so that the dilution in each cell was double that in the previous one, i.e., 1 in 2, 1 in 4, 1 in 8, 1 in 16, etc. Thus, serial dilution was formed on a microplate.

The microplate was shaken for 5 mins. at 37° C. to cause an antigen-antibody response. Thereafter, the microplate was allowed to stand at 4° C. overnight. The agglutination patterns formed were observed the next morning to obtain the titer values indicated in Table 4.

TABLE 4

| Microcapsule Reagent | Potency of Antibody | |
|---|---|---|
| | Human IgG | Control (normal rabbit serum) |
| A | 2560 | $\leq 20$ |
| B | 1280 | $\leq 20$ |
| C | 160 | 80 |
| D | $\leq 20$ | $\leq 20$ |
| E | 640 | $\leq 20$ |

With Microcapsules A, B and E, specific agglutination occurred between each of Microcapsules A, B and E and human IgG. On the other hand, non-specific agglutination occurred between Microcapsule C and human IgG. With Microcapsule D, all microcapsules were sedimented, which means the pattern was negative.

With Microcapsule D, both of the serial dilutions were sedimented, showing a negative pattern.

As can be seen from the above results, Microcapsules A, B and E, which were prepared in the presence of high molecular weight substances containing anionic groups in the side chain thereof, such as sodium polystyrene sulfonate or maleic anhydridemethyl vinyl ether copolymer, were negatively charged at a zeta potential more negative than −20 mV in the pH range of from 3.5 to 5.5 so that anti-human IgG could be sensitized by the microcapsules and thus a reagent for detecting IgG could be prepared. With Microcapsules C and D, in which no high molecular weight substance containing anionic groups in the side chain thereof was employed, the zeta potential thereof was almost zero in the pH range of from 3.5 to 5.5 so that the microcapsules could not be negatively charged sufficiently to senstize anti-human IgG.

EXAMPLE 3

Sensitization with Treponema Pallidum (Nichols Strain)

In a manner similar to Example 2, Microcapsules A, B, C and D were treated with glutaraldehyde to obtain individual dispersions thereof. The pH of the resulting dispersions was 5.3.

Treponema pallidum (Nichols strain) was inoculated and proliferated in the seminal vesicle of a rabbit. The seminal vesicle was removed 8 to 12 days after inoculation, sliced and then immersed in a 2.2% sodium citrate aqueous solution to exude mycellium out. Thereafter, the exudate was subjected to fractional centrifugal separation to collect the mycellium in an amount of $10^8$/ml. The thus collected mycellium was ground for 10 mins. using a sonic grinder (manufactured by Otake Seisakusho Co.). After centrifugal separation at 12,000 r.p.m., the resulting precipitate was diluted by 10 times the precipitate volume with a saline solution. 2 ml. of the resulting dilution product was mixed with 2 ml. of each of the microcapsules treated with glutaraldehyde. The mixture was incubated at 37° C. for 1 hr. After standing for 15 hrs. at 4° C., the mixtures were washed twice with a saline solution containing 0.2% glycine and again dispersed in a 0.15M phosphate-saline solution containing 2 ml. of 3% bovine serum albumin to prepare a reagent for detecting an antibody to syphilis in the serum.

Next, sera of patients with syphilis that were positive in both the FTA-ABS test and the TPHA test, and sera of volunteers showing negative in these tests, were diluted by 10 volume times with a 0.15M phosphate buffer-saline solution (PBS), respectively. Using 25 μl. of the thus diluted sera, serial dilutions with PBS were prepared on a microplate, respectively. Then, 25 μl. samples of each of the microcapsules sensitized by the ground mycelium component of Treponema pallidum (Nichols strain) were taken out by a dropper and dropwise added to cells on the microplates, thereby forming serial dilutions of the sera tested, respectively. The microplates were shaken for 5 mins. to cause an antigen-antibody response. After standing at 4° C. overnight, the precipitation patterns formed were observed the next morning.

No agglutination was caused with both Microcapsules A and B in the volunteers' sera. In the sera from the patients with syphilis, agglutination patterns were clearly observed with cells up to a 2560 time dilution.

However, in the case of using Microcapsules C and D, no agglutination occurred in the volunteers' sera or in the patients' sera.

While the invention has been described in detail and with reference to specific embodiments thereof, it will be apparent to one skilled in the art that various changes and modifications can be made therein without departing from the spirit and scope thereof.

What is claimed is:

1. A process for producing a microcapsule reagent for passive agglutination which comprises binding an antigen or antibody onto an exterior wall surface of a microcapsule, which microcapsule comprises a wall material having encapsulated therein an oily substance as a core and which microcapsule has an average particle size of 0.1 to 30 microns and which microcapsule is negatively charged in an acidic solution.

2. The process of claim 1 wherein said microcapsule negatively charged possesses a zeta potential more negative than −20 mV.

3. The process of claim 1 wherein said binding is effected through a cross linking agent.

4. The process of claim 3 wherein said cross linking agent is selected from the group consisting of a dialdehyde, a water-soluble carbodiimide, an isoxazolium salt, an imide ester, a diisocyanate and a halonitrobenzene.

5. The process of claim 1 wherein said acidic solution has pH of from 3.0 to 5.5.

6. The process of a claim 1 wherein said wall surface comprises a member selected from the group consisting of polyvinyl sulfates, polyvinyl sulfonates, polystyrene sulfonates, polyacrylic acids, maleic anhydride copolymers and alkali metal salts thereof.

7. The process of claim 1 wherein the amount of said wall is in the range of 2 to 50 weight percent based on the weight of the oily substance which comprises the core.

8. The process of claim 1 wherein said microcapsules have a size of 0.5–10μ, exhibit a zeta potential of −40 to −60 mV and wherein said binding of said antigen or antibody is at a pH of 4 to 5.5 and wherein the core substance is completely enclosed by the capsule walls and hence does not directly affect the antigen or antibody.

9. A process for producing a microcapsule reagent passive agglutination which comprises binding an antigen or antibody onto an exterior wall surface of a microcapsule, which microcapsule comprises a wall material having encapsulated therein an oily substance as a core and which microcapsule has a size from 0.1 to 30 microns, said microcapsule being prepared in the presence of a high molecular weight compound containing an anionic group(s) in a side chain thereof.

10. The process of claim 9 wherein said anionic group(s) is/are selected from the group consisting of a sulfonic acid group, a sulfuric acid group, a carboxylic acid group, a maleic acid group, and a group derived from a salt thereof.

11. The process of claim 9 wherein said high molecular weight compound has a molecular weight of from about 10,000 to about 1,000,000.

12. The process of claim 9 wherein said microcapsules have a size of 0.5–10μ, exhibit a zeta potential of −40 to −60 mV and wherein said binding of said antigen or antibody is at a pH of 4 to 5.5 and wherein the core substance is completely enclosed by the capsule walls and hence does not directly affect the antigen or antibody.

13. The process of claim 1 or claim 9 wherein said wall material is selected from the group consisting of a protein, a polyamino acid, a polyacryl amide, a polyamide, a polyurethane, a polyurea, a melamine, cellulose and derivatives thereof, gum arabic and starch.

* * * * *